(12) United States Patent
Dobler et al.

(10) Patent No.: US 7,926,734 B2
(45) Date of Patent: Apr. 19, 2011

(54) PRESCENTED AND CUSTOM SCENTED CARD INSERT

(75) Inventors: Sven Dobler, Huntington, NY (US); Jonathan Millen, East Northport, NY (US); Neal Harris, Los Angeles, CA (US)

(73) Assignee: Orlandi, Inc., Farmingdale, NY (US)

(*) Notice: Subject to any disclaimer, the term of this patent is extended or adjusted under 35 U.S.C. 154(b) by 162 days.

(21) Appl. No.: 12/321,567

(22) Filed: Jan. 22, 2009

(65) Prior Publication Data

US 2009/0127350 A1    May 21, 2009

Related U.S. Application Data

(63) Continuation of application No. 10/873,989, filed on Jun. 21, 2004, now abandoned.

(60) Provisional application No. 60/480,318, filed on Jun. 23, 2003.

(51) Int. Cl.
A24F 25/00 (2006.01)
(52) U.S. Cl. ............................ 239/52; 239/55
(58) Field of Classification Search .................. 239/42, 239/43, 47, 52–56; 283/117
See application file for complete search history.

(56) References Cited

U.S. PATENT DOCUMENTS

| | | |
|---|---|---|
| 3,627,325 A | 12/1971 | Breslow |
| 3,930,696 A | 1/1976 | Hight et al. |
| 4,056,228 A | 11/1977 | Rosenkrantz et al. |
| 4,155,500 A | 5/1979 | Dutcher |
| 4,168,550 A | 9/1979 | Lindauer |
| 4,208,012 A | 6/1980 | Dutcher |
| 4,209,864 A | 7/1980 | Lindauer |
| 4,279,373 A | 7/1981 | Montealegre |
| 4,280,649 A | 7/1981 | Montealegre |
| 4,615,486 A | 10/1986 | Konicek |
| 4,619,383 A | 10/1986 | Konicek |
| 4,632,310 A | 12/1986 | Konicek |
| 4,759,510 A | 7/1988 | Singer |
| 4,809,912 A | 3/1989 | Santini |
| 4,858,831 A | 8/1989 | Spector |
| 4,925,102 A | 5/1990 | Jones et al. |
| 4,957,246 A | 9/1990 | Kantor |
| 5,372,303 A | 12/1994 | Paul |
| 5,494,218 A | 2/1996 | Armand |
| 5,503,332 A * | 4/1996 | Glenn ............................. 239/56 |
| 5,624,025 A | 4/1997 | Hixon |
| 5,660,313 A | 8/1997 | Newbold |
| 5,782,409 A | 7/1998 | Paul |
| 5,857,621 A | 1/1999 | Poulos |
| 6,000,658 A | 12/1999 | McCall, Jr. |
| 6,575,383 B2 | 6/2003 | Dobler et al. |
| 2004/0065748 A1 * | 4/2004 | Sada ............................. 239/34 |

* cited by examiner

*Primary Examiner* — Davis Hwu
(74) *Attorney, Agent, or Firm* — Paul M. Denk

(57) ABSTRACT

The present disclosure provides a device sized for insertion into an inner tube of a roll of paper towels or toilet paper comprising a insert card absorb a fragrance and which is bendable, the insert allowing fragrance to emit by evaporation from the insert into the air and an outer packaging for containing the insert card, the packaging being a substantially impervious moisture and odor barrier.

6 Claims, 4 Drawing Sheets

PRESCENTED AND CUSTOM SCENTED CARD INSERT

CROSS-REFERENCE TO RELATED APPLICATION

This continuation application claims priority to the non-provisional patent application having Ser. No. 10/873,989, which was filed on Jun. 21, 2004, now abandoned, which claims priority to the provisional patent application having Ser. No. 60/480,318, which was filed on Jun. 23, 2003.

BACKGROUND OF INVENTION

Over the years, there have been many inventions and attempts made to mask bathroom or kitchen odors and the files are replete with patents that deal with dispensers, paper holders, spindles and odorous fragrance carriers. Many of these inventions are elaborate, even motor driven, battery operated, complicated and costly devices. Producers of commercial toilet paper have attempted to address this issue by adding a dose of fragrance on the inside of the tube carrying the tissue. This works quite well, but there are several drawbacks: For one, fragrance can dissipate over time in distribution before it reaches the end customer. Secondly, increasing the fragrance load or dosage to compensate for this loss is only possible to some extent, given the issue of multiple chemical sensitivity and allergies; if the tissue paper carries too much fragrance, skin sensitivity and rashes could develop from repeated skin contact. Thirdly, while some customers may like some pre-scented aromas, others may object to a particular fragrance. This limits the marketability of pre-scented tissue papers. Fragrance is therefore almost never found on kitchen towels where it may be used for food contact. Many people therefore also choose to buy unscented toilet tissue and rely on other fragrance air freshener devices in the bathroom.

Various styles of air freshener systems have been available in the prior art. An example can be seen in the U.S. Pat. No. 4,632,310 to Konicek, which describes a door activated air freshener system that uses motion control valves to deposit fragrance onto paper pads within a specially constructed device.

Additional U.S. Pat. Nos. 4,619,383 and 4,615,486 offer additional variations on the door-activated system.

U.S. Pat. No. 4,858,831 to Spector describes an elaborate air-filled device with jet openings and pressurized chambers that when hand actuated, expel a pulse of fragrance into the atmosphere.

U.S. Pat. No. 4,280,649 to Monealegre, and also U.S. Pat. Nos. 4,279,373, 4,208,012 and 4,155,500, described a variety of air freshener cartons that are free standing or can be wall mounted and exhibit perforated sleeves, folded flaps or other carton constructions that can be adjusted to allow more or less of a fragranced air freshener material to be released.

U.S. Pat. Nos. 4,168,550 and 4,209,864 to Lindauer, and U.S. Pat. No. 4,056,228, to Rosenkrantz, all describe elaborate aroma emitting attachments to the toilet that activate by flushing.

Elaborate paper holder devices for air fresheners have been described in a multitude of patents. U.S. Pat. No. 5,624,025 to Hixon, describes a multi-purpose toilet tissue dispenser that incorporates a night light, pencil holder, a means for holding an air freshener, and an attachment device for mounting onto a wall.

U.S. Pat. No. 6,000,658, to McCall, describes a roll spindle and hand ratchet mechanism that activates a music box, a fragrance dispensing apparatus, an audio tape player, and a night light.

U.S. Pat. No. 4,957,246, to Kantor, describes a toilet roll covering that is wall mounted or free standing and essentially adds an embellishment feature by incorporating a lace pouch that can hold a scented potpourri. Hight, et al., U.S. Pat. No. 3,930,696, describes a multi-compartment cabinet for containing storage roll tissue in one compartment and an air freshener device in another compartment.

U.S. Pat. No. 5,857,621 to Poulos, describes a tissue paper scenting and storage device having a two-part interior chamber sized to accommodate multiple rolls of paper in a sealed environment to preclude malodorous contamination, and also incorporating a ventilated top section that can hold an air freshener that scents the stored tissue paper in the compartment below.

U.S. Pat. No. 5,660,313, to Newbold, describes a pre-moistened toilet paper and dispenser that attaches to a conventional paper roll dispenser or can be separately mounted. This device is closed and allows pre-moistened towels to remain moist and said towels may contain 1% perfume fragrance.

There are also a multitude of prior art inventions that relate to the actual spindle element. U.S. Pat. No. 4,925,102 to Jones, describes a perforated, elongated tubular housing that can contain fragrance material within a central chamber. The patent to Armand, U.S. Pat. No. 5,494,218, describes a spool for rotatably supporting a roll of toilet paper and dispensing a fragrance from opposed ends of the spool, by compressing and squeezing a fragrance material out of the spool and onto the inner tubing of the paper roll. Singer, U.S. Pat. No. 4,759,510, describes a similar device that consists of three components: a coiled spring and two plastic molded pieces that are vented and have interlocking tongues and slots which allow the components to be joined. Singer further describes the inclusion of scented pellets within this spindle that can emit fragrance as the spindle is rotated.

The fragrance carrier itself also is the subject matter of many patents. U.S. Pat. No. 4,809,912, to Santini, describes a membrane-gel diffusion device that allows for the controlled release of fragrance gel through a membrane material.

Johnson Wax is currently marketing a product under the trademark "Spin Fresh," which involves a fragrance gel membrane product in a custom made vented spindle construction. This product is meant to replace the existing spindles in home paper holders. The fragrance gel load in this product is 4 grams, and the active fragrance load is between 5% and 10%.

All of the above prior art patents are more or less cumbersome to assemble and use. Many are very elaborate and costly to manufacture as they incorporate to varying degrees electric motors, valves, pressurized containers, ratchet handles and gears, electronics, wooden cabinets, batteries, moving parts, injection molded components, springs, mounting brackets, gels, or complicated membrane packaging. The initial cost to purchase and later maintain the refills is relatively high. Many of these devices require assembly and mounting or disassembly or modification of existing tissue and paper roll holders.

SUMMARY OF INVENTION

The current invention seeks to overcome the above mentioned issues of cost and offer better user friendliness and ease of application for home air freshener use.

In this invention, the preferred embodiment prescribes the use of a 120# commercial blotting paper which may first be printed with a graphic design and/or instructions for use.

It will become obvious to those skilled in the art, that many paper substrates such as commercial Cover Stocks, SBS or beverage board type papers could be readily used as a substitute. The only criteria for the insert material is that it is absorbent enough to carry a sufficient fragrance load and be pliable and thin enough to conform to the inside of the tube and spindle space.

A fragrance coating is then applied to the insert by roller application, spraying, silk screening, flexography or bath saturation. This coating includes common fragrance oil ingredients as made by companies such as Belmay, IFF and Givaudan Roure. These fragrance oils can be modified to achieve the desired end result. One formulation adds polymers to thicken the fragrance and create a thicker coat weight which will also reduce the rate of evaporation. Another formulation may include plastisizing agents that create a scented film-like coating on the paperboard, again retarding the evaporation process. Other formulations that can retard the evaporation and therefore help achieve a longer lasting product, include dipropyleneglycol (DPG), diethylphthylate (DEP) and other common fixatives known by those skilled in the art of fragrance chemistry. On the other hand, additives such as denatured alcohol (39 C) may be added to create more lift and speed up the evaporation process, providing a stronger initial fragrance impact, but typically a shorter lasting product.

The paperboard is then die-cut and perforated ¼" (2/inch) long lines spaced approximately ⅝" apart. Either flatbed or rotary die-cutting is suitable. This will allow the insert to form and bend around the interior spindle and will also allow a customer to tear off a section to allow a better fit or a reduced fragrance impact. While the ⅝" spacing and ¼" long perforations are ideal, it is also obvious that a different spacing and tooth pattern could be envisioned by those skilled in the art.

The above finished product can then be packaged in many conventional ways, including blister packing, pouch packing, or cartoning. These packages can incorporate resealable features so that after one insert is removed, the others remain protected for future use. The primary packaging should provide sufficient odor and fragrance barrier properties so that the product remains moist and fresh for later use. One common and preferred structure includes PVDC coated polyester.

The principal object of this invention is to bring to market and commercialize a low cost, easy and safe method of allowing a customer to add scent to their bathroom or kitchen, without having to replace existing paper or tissue roll holders or interior spindles. Another object of this invention is to allow customers to dose the strength of the freshening device by inserting either a section of one insert or several fragrance inserts into the tube around the spindle. Another object is to provide a customer a wide array of fragrance choices in the after-market purchase of toilet and paper tissue.

Still, another principal object of this invention is to allow a customer to spray-apply their own personal body cologne, perfume or aromatherapy oil on an unscented insert, thereby customizing the product to their personal fragrance preferences.

DESCRIPTION OF PREFERRED EMBODIMENT

Figure 1:
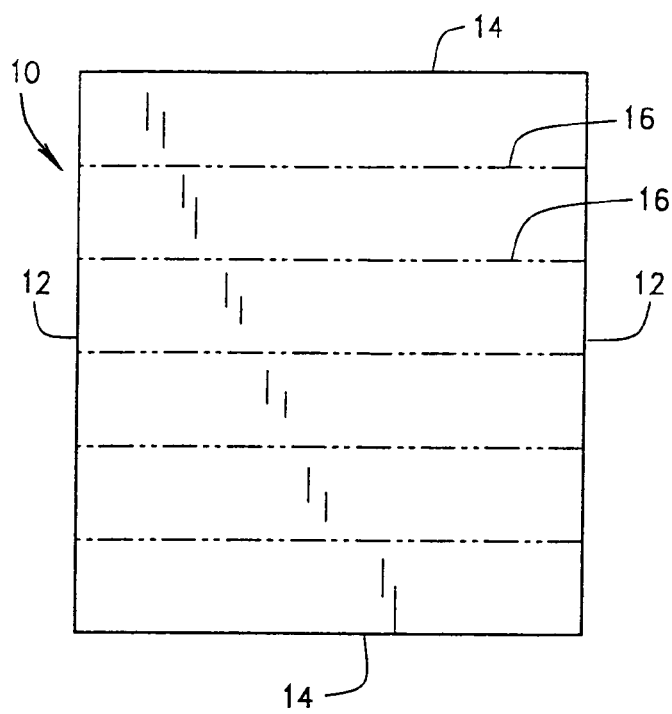
FIG. 1 is a perspective view of a prescented and custom scented card insert of the present invention, when flat.
Figure 2:
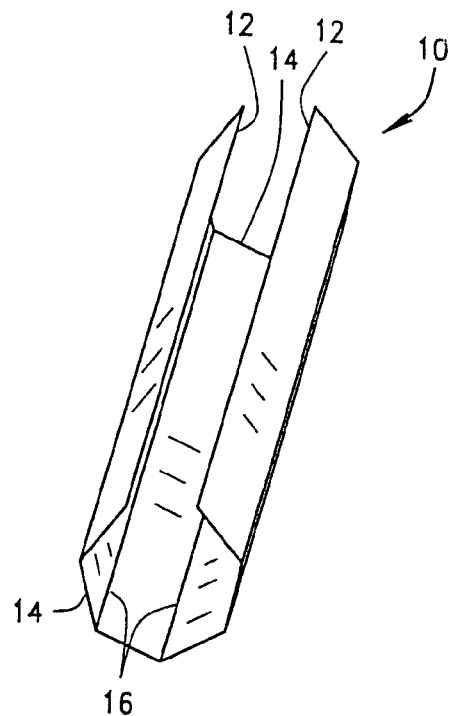
FIG. 2 is a perspective view of the card insert when rolled for insertion into a toilette paper tube, according to an embodiment of the present invention.

Referring initially to FIGS. 1 and 2, an insert card 10 is provided which is capable of absorbing a fragrance. Preferably, the card 10 is made from 120# blotting paper. The card can also be made from a non-woven, porous materials or synthetic carrier materials such as extruded polyethylene or molded polystyrene based materials that will hold fragrance and allow evaporative emittance of the fragrance. Such materials include, for example Tyvek® sheeting available from E.I. duPont de Nemours & Co.; Teslin®, microporous sheeting available from PPG Industries, Inc. of Pittsburgh, Pa.; Porex®, porous plastic sheeting available from Porex Technologies Corp. of Fairburn, Ga., Celwa paper pads, available from John H. Willig dib/a Celwa Products Co. of New York, N.Y.

The card 10 has a first pair of opposed sides 12 and a second pair of opposed sides 14. If the card 10 is square, the sides 12 and 14 are of the same length. On the other hand, if the card is rectangular, the sides 12 are long sides and the sides 14 are short sides. Perforation lines 16 extend between the opposing sides 12 of the card 10. Each perforation is preferably about ¼" long with 2 perforations per inch. The lines 16, which are generally parallel to each other, are preferably spaced apart about ⅝". The perforations are formed preferably by die-cutting, preferably with a flat bed die cutter. However, the perforations can also be formed using a rotary die-cutter. Although shown as a rectangle, the insert can be die-cut shape to a desired shape, or have die-cut perorations so that the insert can be punched out from a blank in a desired shape.

As can be seen in FIG. 2, the perforated lines 16 allow for the card 10 to be easily rolled or formed to a size in which it can be received within a tube of paper towels, toilette paper, or the like. For example, if the card 10 is to be inserted in a paper towel tube, the card 10 preferable is 9"×5". If the card 10 is to be inserted in a toilette paper tube, the card 10 is preferably 5"×4½". The perforated lines also allow for the insert to be reduced in size by the consumer. Thus, for example, larger sheets could be provided, which are then cut in half by the consumer.

Preferably, the card 10 is printed with graphics. The graphics can be ornamental or provide instructions for use of the cards. Such graphics can be printed on the card 10 either before or after the perforations are formed. One method for printing graphics is by sheet fed lithographic offset.

The insert can be provided as either scented or unscented. If provided as an unscented insert, the consumer can apply his or her own fragrance to the insert by either spraying the insert or dipping the insert in a desired fragrance (i.e., a perfume, cologne, etc.)

If the insert is pre-scented, the fragrance can be applied either by roller or spray application. The fragrance formulation preferably comprises fragrance oil and a DPG diluent. The preferred fragrance load is approximately 2.0 grams per toilet tissue insert and 4.0 grams for paper towel inserts (or about 0.09 gm/in2). The fragrance applied can include, or be comprised of microencapsulated fragrance oil. This will allows for improved shelf life of the scented insert and will provide a refreshing feature to the insert.

The evaporation of the fragrance from the insert can be either enhanced or retarded. Evaporation can be retarded by applying a second film of plastisizing agents after the fragrance has been applied to the insert. Polymers, such as dipropyleneglycol (DPG), diethylphthylate (DEP) or similar solvents, can also be added to the fragrance formulation to thicken the fragrance coating to achieve a heavier coating weight. This will also retard the rate of evaporation of the fragrance from the insert. On the other hand, evaporation enhancers, such as denatured alcohol (39 C) can be added to the fragrance formulation to increase the rate of evaporation of the fragrance from the insert.

The cards 10 are formed as individual cards. Preferably, they are packaged in a resealable pouch or bag. The preferred packaging is a three-side seal, PVDC coated polyester, pouch with resealable fold and a hanger hole for peg rack display.

Figure 3:
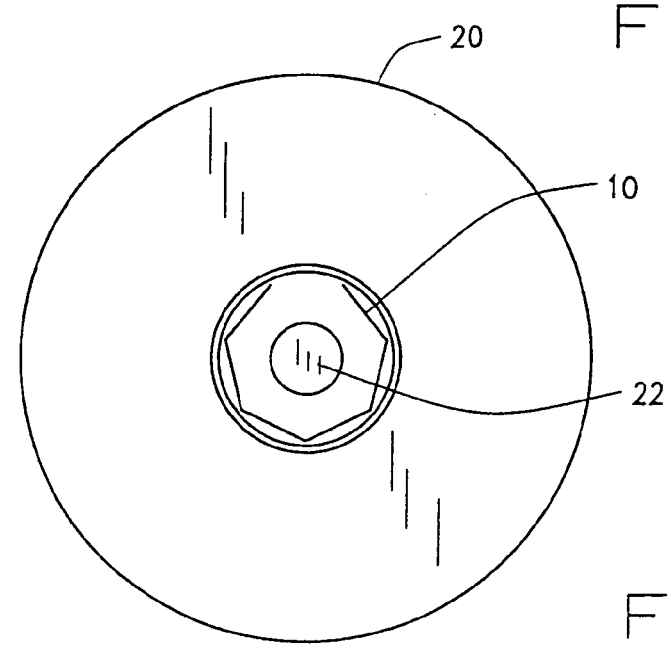
FIG. 3 is a side elevational view of the card insert received in a toilette papertube.
Figure 4:
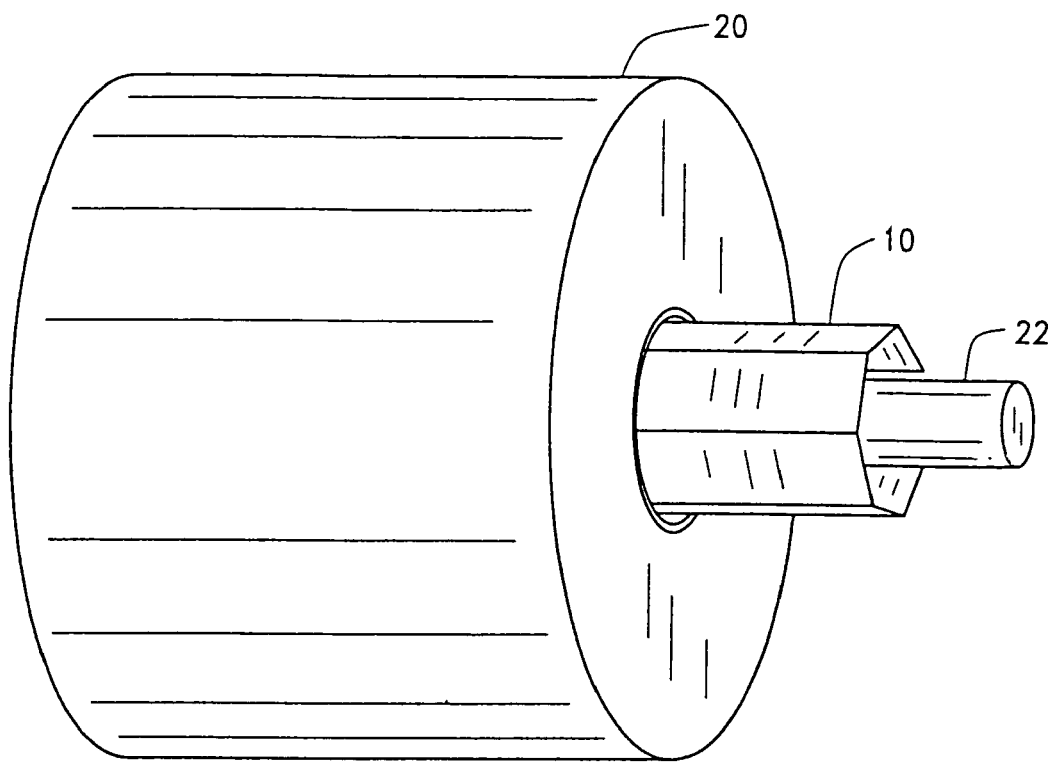
FIG. 4 is a perspective, exploded view of the card insert applied to a toilette paper tube.

FIGS. 3 and 4 show how the scented insert 10 when folded along its lines 16 of perforations may be enclosed within a roll 20 of tissue. As can be seen, the insert or card 10 is received around the internal roller or spindle 22 about which the roll 20 rotates, and within the central tube of the roll 20. In this location, the scented insert card 10 can provide for the emission of a pleasing fragrance. The same may also be applied, as for example, within a roll of paper towels, or the like.

Figure 5:
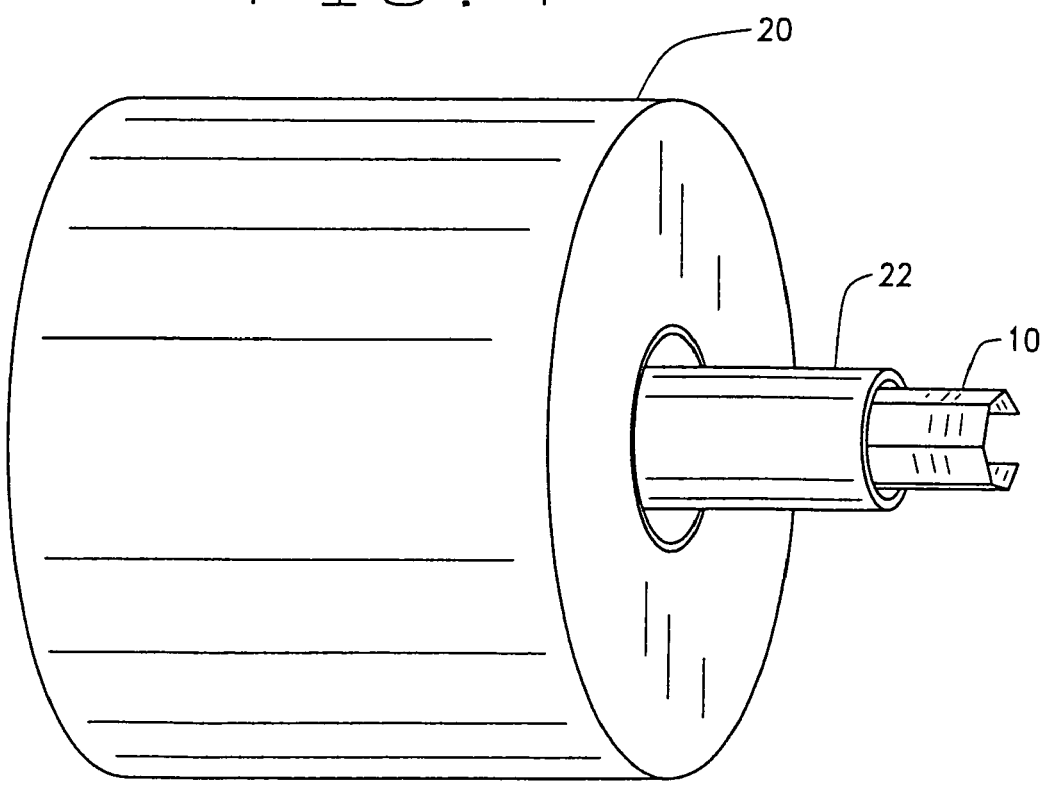
FIG. 5 is a perspective, exploded view showing the card insert being received in the spindle about which a toilette paper roll spins.

FIG. 5 shows how an alternative example of usage of the scented insert card 10 can be located within the cavity of the spindle 22, for holding a roll 20 of tissues, or other paper, and used for the same purpose of providing the release of a pleasing fragrance.

Figure 6:
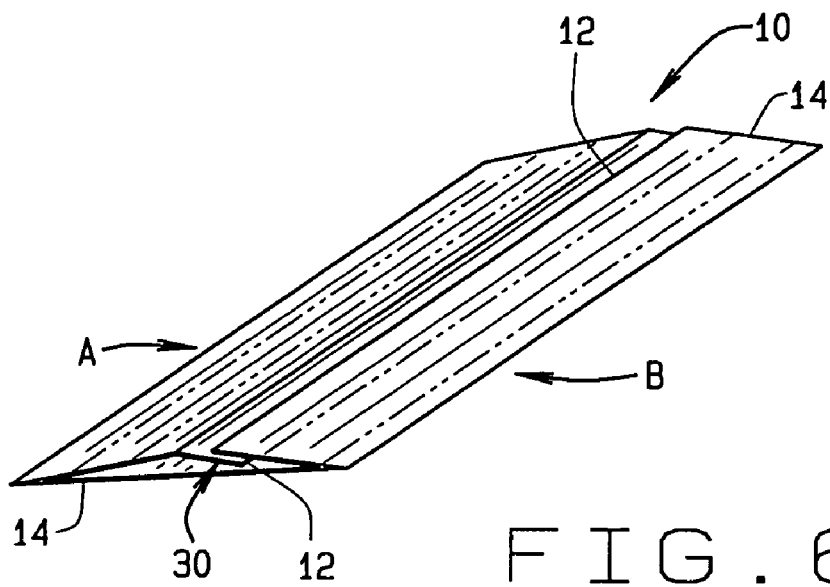
FIG. 6 is a is a perspective view of the card insert when flattened for packaging according to an embodiment of the present invention.
Figure 7:
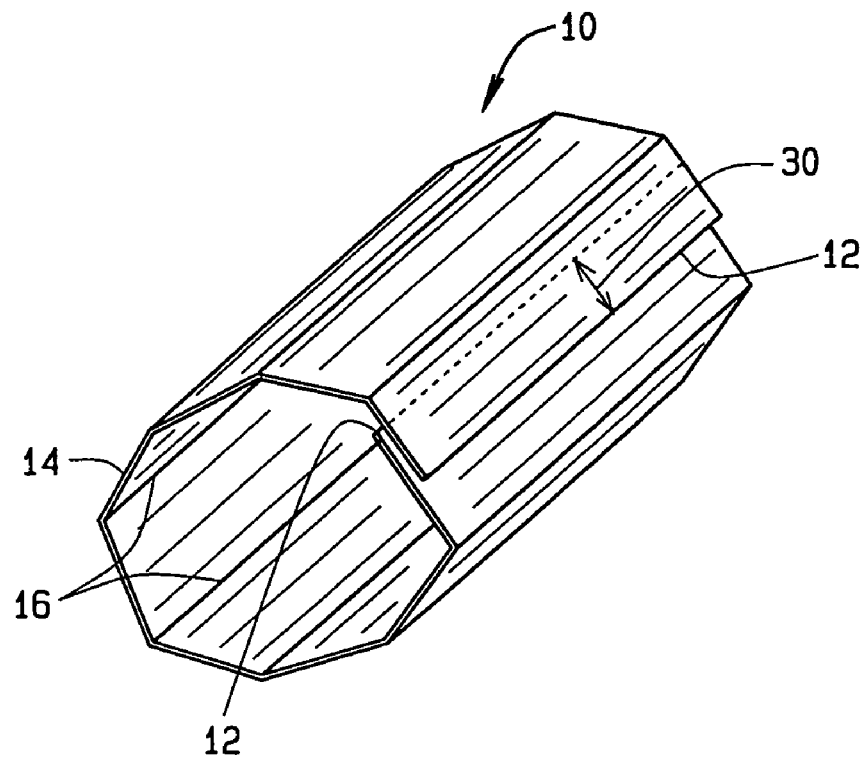
FIG. 7 is a perspective view of the card insert adhered at its ends for insertion into a toilette paper tube, according to an embodiment of the present invention.
Figure 9:
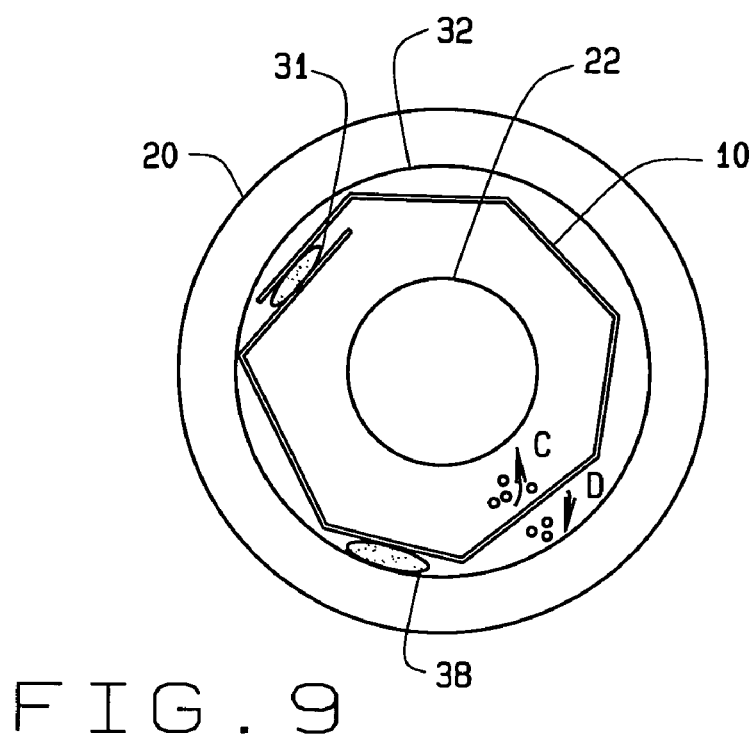
FIG. 9 is a side view of a card insert and outer packaging placed in service within a roll of toilet paper or pare towels according to an embodiment of the present invention.

FIG. 6 shows an alternative embodiment of the present invention wherein the insert card 10 is folded over upon itself and the first pair of opposed sides 12 are overlapped by a distance 30 and adhered to one another with an adhesive 31 (FIG. 9). In this manner the insert card 10 is provided to an end user in a flattened state. By pushing on the insert card 10 in the direction of arrows A, B the user can force the flattened card 10 into a hollow polygonal configuration similar to that described above with respect to FIG. 2 and shown in FIG. 7.

Figure 8:
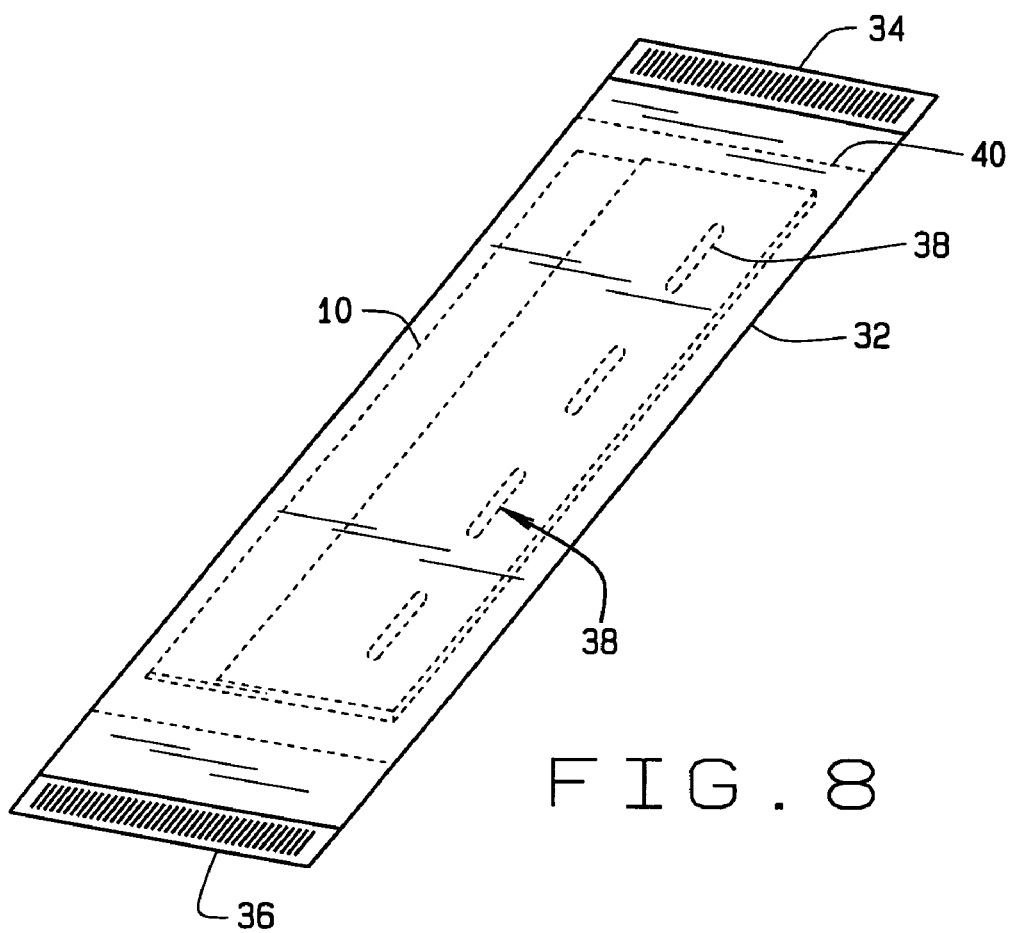
FIG. 8 is a perspective view of the card insert packaged within an outer packing, according to an embodiment of the present invention.

FIGS. 8 and 9 show a preferred manner in which the insert card 10 of the present invention is shipped and used. Referring to FIG. 8, an outer packaging 32 is provided that envelopes the insert card 10. The outer packaging 32 is preferably a substantially impervious odor and moisture barrier, such as Dupont Mylar (PvdC coated polyester), cellophane or other common packaging materials. Ends 34, 36 of the packaging 32 are sealed. Optionally, drops of adhesive 38 attach the insert card 10 to the packaging material 32. Finally, perforations 40 parallel to each end 34, 36 and on opposite sides of the insert card 10 are provided.

Referring to FIG. 9, the present invention in placed in use by tearing off the ends 34, 36 (FIG. 8) of the outer packaging 32 along the perforations 40. Next, by squeezing on the insert card 10 in the direction of the arrows A, B, the insert card 10 is expanded into a generally polygonal body as shown in FIG. 9. Next, a tissue roll spindle 22 is placed through the center of the generally polygonal insert card 10. Finally, a tissue paper roll 20 is placed around the outer packaging 32 and the roll 20 placed in service. In use, the insert card 10 releases fragrance between the insert card 10 and the outer packaging 32 and between the spindle 22 and the insert card 10, as shown by arrows C, D. Alternatively, the tissue spindle could be placed around the insert card 10 and it outer packaging 32, as described with respect to FIG. 5 without departing from the scope of the present invention.

Variations or modifications to the subject matter of this invention may occur to those skilled in the art upon reviewing the invention as described herein. Such variations, or modifications, to this disclosure, are intended to be encompassed within the scope of the invention as provided and disclosed herein.

We claim:

1. A device sized for insertion into an inner tube of a roll of paper towels or toilet paper used by a consumer, comprising:
   an insert card capable of absorbing a fragrance and which is bendable, the insert card allowing fragrance to emit by evaporation from the insert card into the air; said card having a material folded upon itself, a plurality of perforated lines extending generally parallel to an edge of the insert, and opposing edges joined by an adhesive wherein said perforated lines guide said insert card into a tubular form upon unfolding;
   outer packaging for containing the insert card when folded and unfolded, said packaging being a substantially impervious moisture and odor barrier, and said packaging allows for a consumer to handle said device without transferring said fragrance to said consumer, wherein said outer packaging is folded to contain said insert card when folded and wherein the outer packaging is perforated at opposite ends such that the opposite ends may be removed from the outer packaging and the outer packing expanded to contain said insert card when unfolded; and
   wherein said insert card is approximately 120 lbs paper, has a rectangular shape, and adheres to the outer packaging with an adhesive.

2. The insert of claim 1 in which the insert is printed with a graphic motif.

3. The insert of claim 1 wherein the insert has a die-cut shape and wherein said perforated lines are die-cut.

4. The insert of claim 1 including the insert having a fragrance formulation at a load of about 0.09 gram per square inch, and the fragrance formulation including at least one of evaporation modifiers, evaporation enhancers or evaporation retardants, thus regulating the evaporation of said fragrance formulation.

5. The insert of claim 1 in which said device is placed either one of around an existing spindle of lesser diameter than said device or inside an existing spindle of greater diameter than said device.

6. A pre-scented insert sized to fit within a central opening of a roll of toilet paper or paper towels to impart a pleasing odor to the roll of toilet paper or paper towels; said insert being used by a consumer, said insert comprising:
   a sheet of absorbent material;
   a load of fragrance applied to the material, said load avoiding staining the consumer yet having strength for detection by the consumer, the fragrance load being approximately 0.09 gm/in$^2$;

outer packaging for containing said sheet loosely, said packaging being substantially impervious to moisture and odor, and said packaging allowing for a consumer to handle said insert without transferring said fragrance to said consumer;

said outer packaging is folded to contain said pre-scented insert when folded and wherein said outer packaging is perforationed at opposite ends such that the opposite ends may be removed from the outer packaging and the outer packaging expanded to contain said insert when unfolded;

said insert including a plurality of perforated lines extending generally parallel to an edge of said insert, said perforated lines guiding said insert into hollow tubular form, and said insert adhering to said outer packaging with an adhesive; and wherein said absorbent material is approximately 120 lbs paper.

* * * * *